United States Patent [19]

Caserio et al.

[11] Patent Number: 4,664,910
[45] Date of Patent: May 12, 1987

[54] COSMETIC COMPOSITION

[75] Inventors: Domenico Caserio; Elio Mignini, both of Milan, Italy; Micheline M. J. Davot, Paris, France

[73] Assignee: Lever Brothers Company, New York, N.Y.

[21] Appl. No.: 339,912

[22] Filed: Jan. 18, 1982

[30] Foreign Application Priority Data

Jan. 26, 1981 [IT] Italy ............................ 67097 A/81

[51] Int. Cl.[4] ............................................. A61K 7/06
[52] U.S. Cl. .............................. 424/70; 424/DIG. 4
[58] Field of Search ............... 424/DIG. 4, 365, 240, 424/70, 238, 358

[56] References Cited

U.S. PATENT DOCUMENTS

| | | | |
|---|---|---|---|
| 1,483,152 | 2/1924 | Altwegg | 424/240 |
| 2,460,776 | 2/1949 | Vincent | 424/240 X |
| 2,624,685 | 1/1953 | Horvath | 424/240 X |
| 2,890,152 | 6/1959 | Babcock et al. | 424/240 |
| 3,071,514 | 1/1963 | Phillips et al. | 424/DIG. 4 |
| 3,301,830 | 1/1967 | Nelson et al. | 424/240 X |
| 3,729,560 | 4/1973 | Hagerman | 424/DIG. 4 |
| 3,860,712 | 1/1975 | Ferrari | 424/240 |
| 3,949,087 | 4/1976 | Bacq et al. | 424/DIG. 4 |
| 3,981,996 | 9/1976 | Leigh | 424/243 |
| 3,997,484 | 12/1976 | Weaver et al. | 424/361 |
| 4,017,603 | 4/1977 | Ferrari et al. | 424/238 |
| 4,021,574 | 5/1977 | Bollag et al. | 424/DIG. 4 |
| 4,090,013 | 5/1978 | Ganslaw et al. | 424/81 |
| 4,105,782 | 8/1978 | Yu et al. | 424/DIG. 5 |
| 4,115,313 | 9/1978 | Lyon et al. | 424/DIG. 4 |
| 4,117,222 | 9/1978 | Holst et al. | 424/180 X |
| 4,185,099 | 1/1980 | Sorbini | 424/DIG. 4 |

FOREIGN PATENT DOCUMENTS

| | | | |
|---|---|---|---|
| 2113453 | 12/1971 | Fed. Rep. of Germany | 424/69 |
| 2702781 | 9/1978 | Fed. Rep. of Germany | 424/69 |
| 2747279 | 1/1979 | Fed. Rep. of Germany | 424/240 |
| 981409 | 1/1951 | France | 424/365 |
| 241476 | 1/1964 | Netherlands | 424/240 |
| 937362 | 9/1963 | United Kingdom | 424/61 |

OTHER PUBLICATIONS

Chemical Abstracts, vol. 81, 1974, p. 220, lists Abstract No. 16665d.
Chemical Abstracts, vol. 75, 1971, p. 181, lists Abstract No. 91252w.

Primary Examiner—Dale R. Ore
Attorney, Agent, or Firm—James J. Farrell

[57] ABSTRACT

A cosmetic composition which is suitable for application to the skin or hair as a powdered product to remove sebum and/or perspiration comprises a cholanic acid derivative and a powder absorbent. Optionally, water and/or other liquid carriers can be incorporated in the composition if it is in the form of a cream, lotion or other liquid or semi-solid product.

3 Claims, No Drawings

COSMETIC COMPOSITION

The invention relates to cosmetic compositions for topical application to the skin or hair.

Normal healthy human skin secretes a natural lubricant known as sebum, which usually serves to keep the skin surface soft, pliable, conditioned and, to some extent, protected.

Sebum, a complex mixture of lipid substances, is secreted from sebaceous glands associated with hair follicles over most of the body surface, in particular the scalp, face, upper chest and shoulders.

Normal healthy human skin also secretes sweat from eccrine and apocrine glands. Eccrine sweat is associated with both the control of body temperature and the excretion of waste products: it consists mainly of water but contains also inorganic and organic components, notably sodium chloride and lactic acid. Apocrine sweat, in addition to water and sodium chloride, also contains odour producing proteins, lipoproteins and lipids.

Whereas the secretion at the skin surface of sebum and sweat represents a normal and necessary bodily function, excessive producton of these secretions can result in a film on the skin surface which is oily or greasy in nature and which can be disliked to the extent that the human subject will go to considerable trouble to remove it, for example by tissue wiping, by excessive washing or by application of make-up, so as to block skin pores from which sebum and sweat are released onto the skin surface.

The removal from or control of lipids on the skin to provide a proper balance whereby the skin remains supple and protected without being excessively greasy has accordingly presented a problem to the cosmetician, and hitherto it has not been possible to strike the proper balance by the simple application of a topical product.

It has been proposed in U.S. Pat. No. 3,860,712 to treat the conditions of acne or seborrhea with a composition comprising urea and an unconjugated bile acid in alcohol media, the composition also optionally containing an antibacterial or lipase inhibitory substance.

It has also been proposed in U.S. Pat. No. 4,017,603 to provide a water-soluble pharmaceutical complex for the treatment of systemic mycotic infections comprising antibiotic partricin and/or an alkyl ester of partricin, together with sodium desoxycholate and/or sodium dehydrocholate.

Although compositions based on either of these prior proposals may be effective in treating acne, seborrhea or mycotic infections, neither is suitable as a cosmetic product for the control of excessive secretions at the skin surface of both sebum and sweat.

It has however now been discovered that by topical application of a special derivative of cholanic acid, together with an absorbent substance, a proper lipid and moisture balance at the skin surface can be achieved, and that the result is relatively long-lasting. In particular, by application of this special derivative and the absorbent once daily to excessively greasy and perspiring skin, surplus lipid material and moisture can be removed without totally defatting or over-drying the skin, so that the skin retains its supple nature for which the natural skin lipids are responsible.

Accordingly, the invention provides a cosmetic composition for topical application to the skin or hair which comprises:

(i) from 0.1 to 20% by weight of a cholanic acid derivative chosen from an hydroxy cholanic acid, an amino acid condensation product with an hydroxy cholanic acid, a salt thereof or mixtures thereof, and (ii) from 5 to 99.9% by weight of a powder absorbent.

When the cholanic acid derivative is an hydroxy cholanic acid, it is preferably lithocholic acid, desoxycholic acid or cholic acid. Condensation products of these acids with amino acids, such as glycocholic acid and taurocholic acid can also be employed.

When the cholanic acid derivative is a salt of an hydroxycholanic acid, the preferred salt is an alkali metal salt of any of the above acids. The preferred salt is a sodium salt. Most preferably, the salt to be employed is sodium desoxycholate.

It is possible to employ in the composition of the invention mixtures of cholanic acid derivatives, as herein defined.

The cholanic acid derivative should be present in the composition according to the invention in an amount which forms from 0.1 to 20%, preferably from 1 to 10%, most preferably from 2 to 8% by weight of the composition.

It should be explained that use of less than 0.1% by weight of the cholanic acid derivative in the composition will not enable the user to obtain any noticeable benefit in terms of removing sebum from the skin, whereas use of more than 10% by weight of the cholanic acid derivative in a liquid or semi-solid product of the invention may result in excessive removal of natural lipids from the skin surface, with the result that the skin may become excessively dry. Solid products of the invention such as powders and sticks can contain up to 20% by weight of the cholanic acid derivative and are unlikely to result in excessive removal of natural skin lipids unless this figure is exceeded.

The powder absorbent is a powdered substance which will function, when applied to the skin, in particular of the face, in absorbing excess moisture derived from sebaceous secretions and perspiration.

The combined effect of the cholanic acid derivative in complexing some of the lipid material derived from sebaceous secretions and the powder absorber in absorbing also moisture derived from sebaceous secretions and perspiration, is to achieve the desired proper balance of supple, protected skin, which is not excessively greasy nor excessively moist The powder absorbent should have the ability of absorbing at least twice its weight of oil or at least its own weight of moisture. Preferably, the powder absorbent possesses both of these properties.

The capability of a powder adsorber to absorb a sufficient amount of oil and/or a sufficient amount of moisture can be determined, with suitable adaptations, by the method described in German Patent Application No. 2 702 781.

Although the average particle size of the powder absorbent is usually not critical with respect to its ability to adhere to the skin or to absorb moisture at the skin surface, it is preferred that the average particle size does not exceed $100\mu$. Most preferably the average particle size is not greater than $60\mu$ and ideally it is not greater than $30\mu$.

Examples of suitable powder absorbents showing their respective abilities to adsorb oil or water are given in the table below.

| Powder Absorbent | Oil take-up ml/g of substance | Water take-up ml/g of substance |
| --- | --- | --- |
| Rigid urea-formaldehyde foam (ORACID) | 11.11 | 16.6 |
| Silica aerogel (AEROSIL) | 6.0 | 8.7 |
| Magnesium carbonate | 5.4 | 4.03 |
| Magnesium oxide | 3.3 | 2.6 |
| Kieselguhr | 2.8 | 3.2 |
| Kaolin | 2.7 | 1.5 |
| Talc | 2.5 | 1.4 |
| Starch (rice) | 2.1 | 0.75 |
| Titanium oxide | — | 2.3 |
| Zinc oxide | — | 1.1 |

Examples of other powder absorbents, each of which at least has the capacity to adsorb an amount of moisture at least equal to its own respective weight (i.e. having a water take-up value of at least 1), include smectites, dry protein powders and anionic polyelectrolyte absorbent materials.

Examples of smectites, which are swelling clay minerals capable of taking up water or organic liquids between their layers, are montmorillonite, beidellite, nontronite, saponite, sauconite and hectorite. A preferred example of a montmorillonite is BENTONITE.

A preferred example of a dry protein powder is dry collagen powder.

Examples of anionic polyelectrolyte absorbent materials include a cross-linked etherified starch as described in German Application Specification No. 2,702,781 or U.S. Pat. No. 4,117,222; a cross-linked sodium carboxymethyl cellulose as described in U.S. Pat. Nos. 3,589,364, 3,936,441 or 3,965,091; an internally esterified polyelectrolyte as described in U.S. Pat. No. 3,678,031; or a starch-acrylonitrile graft copolymer as described in U.S. Pat. No. 3,997,484 or 3,661,814; or a polyacrylate cross-linked with a polyamide/epichlorhydrin material as described in German Patent Application No. 2,614,662; or a potassium salt of a polyacrylic acid cross-linked by aluminium ions as described in U.S. Pat. No. 4,090,013.

The powder absorbent should be present in the composition according to the invention in an amount which forms from 5 to 99.9%, preferably from 10 to 80% by weight of the composition.

It should be explained that use of less than 5% by weight of the powder absorbent in the composition will not enable the user to obtain any noticeable benefit, whereas use of more than 99.9% by weight of the powder absorbent can result in an unsatisfactory product which will leave greasy or moist skin caked with excess powder.

The composition of the invention can also optionally comprise up to 94.9%, preferably from 10 to 90% by weight of water which will normally form a solvent for the cholanic acid derivative.

The composition of the invention can also optionally comprise a cosmetically acceptable carrier other than water, which is intended to contribute to the uniform distribution of the cholanic acid derivative when the composition is applied topically to the skin, and in this way can complement the function of water, when present, in the composition.

The cosmetically acceptable carrier can include emollients, propellants, organic solvents, humectants and thickeners.

The quantity of carrier optionally employed can constitute the balance of the product, or a smaller proportion than the balance, provided that the carrier is capable of performing its function as herein defined.

In general, it can be stated that the carrier when present will form from 0.1 to 90% by weight of the composition.

The compositions according to the invention can contain ingredients other than those already mentioned, depending on the form of the intended product. It is, for example, possible to include moisturisers, antiseptics, preservatives, antioxidants, anti-caking agents, emulsifiers, perfumes, colouring agents and detergents.

Cosmetically and Pharmaceutically Active Ingredients

The composition according to the invention can also be employed as a vehicle for a wide variety of cosmetically or pharmaceutically active ingredients, particularly ingredients which have some beneficial effect when applied to the skin or hair.

The composition thus provides a means whereby such active ingredients can be diluted, dispersed, conveyed to and distributed on the skin surface at an appropriate concentration.

Especially preferred examples of active ingredients include moisturisers such as: sodium pyrollidone carboxylate, sodium lactate, lactic acid, triethanolamine lactate and sodium chloride, and anti-acne agents such as ethyl lactate.

Examples of other active ingredients that can also be employed include sunscreen agents, germicides, deodorants, antiperspirants and healing agents.

Preparation of the Composition

The invention also provides a process for the preparation of a cosmetic composition for topical application to skin or hair which comprises blending a water-soluble cholanic acid derivative, as herein defined, with a powder adsorbent, the cholanic acid derivative forming from 0.1 to 20% by weight of the composition. When water is to be incorporated in the composition, it is preferred first to form a solution of the water-soluble cholanic acid derivative in water, and then to blend this solution with the powder absorbent, optionally together with a cosmetically acceptable carrier other than water, to form a liquid composition.

Product Forms

The compositions of the invention can be formulated as liquids, for example as a lotion for use in conjunction with an applicator such as a roll-ball applicator, or a spray device such as an aerosol can containing propellant, or a container fitted with a pump to dispense the liquid product. Alternatively, the compositions of the invention can be solid or semi-solid, for example powders, moulded sticks, creams or gels, or powder shampoos or hair conditioners, for use in conjunction with an applicator such as a powder sifter or a stick applicator, or simply a tube, bottle or lidded jar.

The invention accordingly also provides a closed container containing a cosmetic composition as herein defined.

Use of Compositions of the Invention

Compositions of the invention are intended especially for topical application to human skin, in particular when the skin surface or the hair has become excessively moist and/or greasy due to an accummulation of sebum and/or sweat.

Topical application of the composition will accordingly reduce or remove altogether the superficial 'grease' and/or moisture without unduly defatting the skin. The skin will remain in a healthy pliable state, usually for several hours, and will not become excessively dry.

Evidence to Support the Effectiveness of Compositions of the Invention

A panel test involving the topical application of an 'oil-free cream' containing sodium desoxycholate, talc and kaolin to the foreheads of volunteer subjects was conducted under the supervision of a dermatologist. The cream was applied to the subjects according to a statistically designed experiment.

In order to ensure uniformity of application, the 'cream' was applied by a technician.

The oil 'oil-free cream' had the following formulation:

|  | % w/w |
|---|---|
| Cholanic acid derivative |  |
| Sodium desoxycholate | 2 |
| Powder absorbers |  |
| Kaolin | 2 |
| Talcum | 11 |
| Other ingredients |  |
| Magnesium silico aluminate | 4 |
| Propylene glycol | 11 |
| Preservative | 0.3 |
| Colour | 0.5 |
| Sodium lauroyl lactylate | 2 |
| Glyceryl monostearate | 3 |
| Fatty acid esters | 4 |
| Perfume | 0.3 |
| Water | 59.9 |
|  | 100 |

The cream was applied to one side of the forehead of each subject, the other side remaining untreated for purposes of comparison and after 2 hours, the skin surface was examined visually by trained assessors for skin greasiness and also assessed objectively by photographing the skin surface, by measuring its brilliance under normal and specular reflected light and by sampling the skin surface lipids. The results recorded were as follows:

1. Visual scoring of skin greasiness

The mean scores were as follows:

|  | Assessor No 1 | | Assessor No 2 | |
|---|---|---|---|---|
|  | Treated Site | Untreated Site | Treated Site | Untreated Site |
| Oil-free cream | 0.37 | 2.63 | 0.47 | 2.74 |

It will be noted that application of the oil-free cream (i.e. treated site) dramatically reduced the visual appearance of greasiness, compared with the area of forehead which did not receive cream treatment (i.e. untreated site).

2. Photographic Assessment

The mean scores based on examination of photographs were as follows:

|  | Treated Site | Untreated Site |
|---|---|---|
| Oil-free cream | 0.55 | 3.13 |

The photographic results agree closely with the visual scoring carried out by two assessors.

3. Brilliancy Measurements (shine)

The mean scores were:

|  | Treated Site | Untreated Site |
|---|---|---|
| Oil-free cream | 2.34 | 3.02 |

An analysis of variance of these results showed that there is a significant difference ($p = 0.001$) between the brilliancy measurement of the treated and the untreated sites.

4. Total lipid analysis

Skin lipids were analysed following application of the oil-free cream by IR Spectography.

The mean scores expressed in arbitrary units were as follows:

| Treated Site | Untreated Site |
|---|---|
| 184 | 531 |

Statistical analysis of these results showed that there was a significant difference ($p = 0.001$) in total lipids between treated and untreated sites.

Conclusion

It can be concluded from the above results that the product containing sodium desoxycholate, talc and kaolin ('oil-free cream') is very effective in reducing skin greasiness and superficial shine.

The invention is also illustrated by the following further Examples.

EXAMPLE 1

This example illustrates a powdered composition according to the invention. The cosmetic powder had the following formulation:

|  | % w/w |
|---|---|
| Cholanic acid derivatives |  |
| Sodium desoxycholate | 3 |
| Sodium cholate | 2 |
| Powdered absorber |  |
| Dry collagen powder | 80 |
| Other Ingredients |  |
| Perfume, colour | 10 |
| Anticaking agent | 5 |

EXAMPLE 2

This example illustrates a powdered composition according to the invention. The cosmetic powder had the following formulation:

|  | % w/w |
|---|---|
| Cholanic acid derivative |  |
| Lithocholic acid | 2 |
| Powdered absorber |  |
| Water-absorbent polymer* | 20 |

| | % w/w |
|---|---|
| Other ingredients | |
| Chalk | 68 |
| Perfume, colour | 5 |
| Anticaking agent | 5 |

*The polymer was that available commercially under the name PERMASORB from National Starch Corporation. It is a potassium salt of a polyacrylic acid cross-linked by aluminium ions and is generally described in U.S. Pat. Specification No 4,090,013.

EXAMPLE 3

This example illustrates a make-up powder and its preparation.

A water phase was prepared by mixing together the following ingredients:

| | % w/w |
|---|---|
| Urea | 3 |
| Water | 20 |
| Methanol | 77 |

An oil phase was similarly prepared by mixing together the following ingredients.

| | % w/w |
|---|---|
| Mineral oil | 60 |
| Decyl oleate | 20 |
| Myristyl alcohol | 5 |
| Isostearic acid | 3 |
| Isopropyl palmitate | 4 |
| Olive oil | 8 |

To 100 parts of the water phase was added 9 parts by weight of the oil phase at a temperature of 10° C. to form a white cream base. Further ingredients were then added and the whole blended to form a make-up powder having the following formulation:

| | % w/w |
|---|---|
| Cream base | 73 |
| Cholanic acid derivative | |
| Sodium glycocholate | 7 |
| Powdered absorbers | |
| Talc | 10 |
| Kaolin | 2.5 |
| Other ingredients | |
| Zinc oxide | 2.5 |
| Titanium dioxide | 3 |
| Burnt Sienna | 2 |

EXAMPLE 4

This example illustrates an aerosol lotion.

The following ingredients were employed to form the aerosol lotion.

| | % w/w |
|---|---|
| Cholanic acid derivative | |
| Sodium desoxycholate | 2.0 |
| Powdered absorber | |
| Silica aerogel (AEROSIL) | 4.0 |
| Other ingredients | |
| Polyethylene glycol 1000 monostearate | 2.4 |
| Lanolin alcohols | 1.0 |
| Linear alcohol lactate | 2.0 |
| Myristyl myristate | 1.5 |
| Cationic detergent | 2.0 |
| Water | 61.1 |
| Alcohol | 12.0 |
| Propellant 12/114 (40:60) | 12.0 |

EXAMPLE 5

This example illustrates the formulation of an all-purpose mask.

The following ingredients were blended to form an all-purpose mask.

| | % w/w |
|---|---|
| Cholanic acid derivative | |
| Taurocholic acid | 5.0 |
| Powdered absorbents | |
| Kaolin | 35.0 |
| Bentonite | 5.0 |
| Other ingredients | |
| Cetyl alcohol | 2.0 |
| Sodium lauryl sulphate | 1.0 |
| Glycerin | 10.0 |
| Nipagin M | 0.1 |
| Perfume | q.s. |
| Water | 41.9 |

EXAMPLE 6

This example illustrates a cosmetic stick which has the following formulation:

| | % w/w |
|---|---|
| Cholanic acid derivative | |
| Desoxycholic acid | 15 |
| Powder absorbents | |
| PERMASORB* | 10 |
| Other ingredients | |
| Vaseline oil | 22.5 |
| Lacer buk wax | 6.5 |
| Castor oil | 7.5 |
| Paraffin oil | 5 |
| Petrolatum | 24 |
| Magnesium carbonate | 4.67 |
| Pigment, anitoxidant | 1.03 |
| Emollient | 3.8 |

*See Example 2.

What is claimed is:

1. A cosmetic composition for topical application to the skin or hair, which comprises:
   (i) from 0.1 to 20% by weight of sodium desoxycholate; and
   (ii) from 5 to 99.9% by weight of a powder absorbent selected from the group consisting of kaolin, talcum and mixtures thereof, the absorbent having the ability to adsorb at least twice its own weight of oil and/or at least its own weight of moisture.

2. The cosmetic composition according to claim 1, further comprising from 10 to 90% by weight of water.

3. A method for reducing superficial grease and moisture on human skin, which comprises the step of applying to the affected area of skin an effective amount to reduce superficial grease and moisture on said human skin of the cosmetic composition according to claim 1.

* * * * *